United States Patent [19]

Stuart

[11] Patent Number: 5,776,730
[45] Date of Patent: Jul. 7, 1998

[54] NEUROSPORA HOSTS FOR THE PRODUCTION OF RECOMBINANT PROTEINS, AND METHODS FOR PRODUCING SAME

[75] Inventor: W. Dorsey Stuart, Kanedite, Hi.

[73] Assignee: University of Hawaii, Honolulu, Hi.

[21] Appl. No.: 573,020

[22] Filed: Dec. 15, 1995

[51] Int. Cl.[6] .......................... C12N 15/63; C12N 1/14; C12N 1/15
[52] U.S. Cl. ........................ 435/69.1; 435/254.4
[58] Field of Search ........................ 435/254.4, 256.8, 435/69.1

[56] References Cited

U.S. PATENT DOCUMENTS

| | | | |
|---|---|---|---|
| 4,486,533 | 12/1984 | Lambowitz | 35/172.3 |
| 4,816,405 | 3/1989 | Timberlake et al. | 435/243 |
| 4,885,249 | 12/1989 | Buxton et al. | 435/172.3 |
| 4,935,349 | 6/1990 | McKnight et al. | 435/69.5 |
| 5,179,003 | 1/1993 | Wolf et al. | 435/69.1 |

FOREIGN PATENT DOCUMENTS

96/29391  9/1996  WIPO.

OTHER PUBLICATIONS

Van den Hondel et al. Heterologous production in filamentous fungi. In: More Genetic Manipulation of Filamentous Fungi. Bennett and Lasure, eds. Academic Press, Orlando, FL. pp. 396–428, 1991.

Archer et al. Strategies for improving heterologous protein production from filamentous fungi. Antonie van Leeuwenhoek. vol. 65, No. 3, pp. 245–250, 1994.

ATCC Catalogue of Filamentous Fungi, 18th Edition. American Type Culture Collection Accession No. 11943. p. 259, 1991.

Dunn–Coleman et al. Commercial levels of chymosin production by *Aspergillus*. Bio/Technology. vol. 9, No. 10, pp. 976–981, Oct. 1991.

Jeenes et al. Heterologous protein production by filamentous fungi. Biotechnology and Genetic Engineering Reviews. vol. 9, pp. 327–367, 1991.

Jones. Tackling the protease problem in *Saccharomyces cerevisiae*. In: Methods in Enzymology. Guthrie and Fink, eds. Academic Press, Inc., NY. vol. 194, pp. 428–453, 1991.

Heiniger et al. Protease secretion in *Neurospora crassa*. Biochemical and Biophysical Research Communications. vol. 60, No. 4, pp. 1425–1432, Oct. 23, 1974.

Lawrence. Classical mutagenesis techniques. In: Methods in Enzymology. Guthrie and Fink, eds. Academic Press, Inc., NY. vol. 194, pp. 273–281, 1991.

Polizeli et al. Pectinase production by *Neurospora crassa*: purification and biochemical characterization of extracellular polygalacturonase activity. Journal of General Microbiology. vol. 137, Pt. 8, pp. 1815–1823, Aug. 1991.

Savtchenko et al. Alkaline protease deficiency in the cr–1 (crisp) mutant of *Neurospora crassa*. Brazilian Journal of Medical and Biological Research. vol. 19, No. 1, pp. 27–32, 1986.

Vazquez–Laslop et al. Characterization of a vacuolar protease in *Neurospora crassa* and the use of gene RIPing to generate protease–deficient strains. The Journal of Biological Chemistry. vol. 271, No. 36, pp. 21944–21949, Sep. 6, 1996.

Bennett et al., "More Genetic Manipulation of Filamentous Fungi," Academic Press, 1991, pp. 396–428.

Guthrie et al., "Methods in Enzymology," Academic Press, 1991, vol. 194, pp. 273–281.

Guthrie et al., "Methods in Enzymology," Academic Press, 1991, vol. 194, pp. 428–453.

Mackenzie et al., "Regulation of Secreted Protein Production by Filamentous Fungi: Recent Developments and Perspectives," Journal of General Microbiology, 1993, vol. 139, pp. 2295–2307.

Stuart, W.D. et al. *Genome* (1988) 30:198–203.

Koo, K. et al. *Genome* (1991) 34:644–651.

Carattoli, A. et al. *Proc Natl Acad Sci USA* (1995) 92:6612–6616.

Yamashita, R.A. et al. *Fungal Genetics Newsletter* (1995 Suppl.) 42A.

Kato, E. et al. *Fungal Genetics Newsletter* (1995 Suppl.) 42 A.

Buczynski, S. et al. *Fungal Genetics Newsletter* (1995 Suppl.) 42 A.

Lindberg, R.A. et al. *J Bacteriol* (1982) 150(3):1103–1108.

Cohen, L. et al. *Archiv Biochem Biophys* (1975) 169:324–330.

Abbott, R.A. et al. *J Bacteriol* (1984) 159(2):505–510.

Hanson, M.A. et al. *Proc Natl Acad Sci USA* (1975) 72(4): 1240–1244.

Peberdy, J.F., *Trends in BioTechnology* (1974) 12:50–57.

*Primary Examiner*—Elizabeth C. Kemmerer
*Assistant Examiner*—Brian Lathrop
*Attorney, Agent, or Firm*—Morrison&Foerster LLP

[57] ABSTRACT

The present invention provides improved host cells for use in producing secreted recombinant proteins, methods of making the improved hosts and uses thereof. The invention specifically provides strains of *Neurospora crassa* which produce reduced levels of extracellular proteases when compared with wild-type *Neurospora crassa*.

2 Claims, No Drawings

NEUROSPORA HOSTS FOR THE PRODUCTION OF RECOMBINANT PROTEINS, AND METHODS FOR PRODUCING SAME

TECHNICAL FIELD

The invention relates to the field of producing recombinant proteins, especially eukaryotic proteins. In particular, the present invention provides improved Neurospora hosts which do not degrade expressed proteins at the same rate as wild-type Neurospora and methods of isolating such hosts.

BACKGROUND ART

The cloning and expression of heterologous genes in bacteria, yeast and fungi have been recognized as potential systems for producing a variety of useful proteins. For example: Lambowitz, U.S. Pat. No. 4,486,533, discloses the autonomous replication of DNA vectors for filamentous fungi by mitochondrial plasmid DNA and the introduction and expression of heterologous genes into Neurospora; Yelton et al., U.S. Pat. No. 4,816,405, discloses tools and systems that enable the modification of important strains of filamentous ascomycetes to produce and secrete large quantities of desired heterologous proteins; Buxton et al., U.S. Pat. No. 4,885,249, discloses the transformation of *Aspergillus niger* by a DNA vector that contains a selectable marker capable of being incorporated into the host *A. niger* cells; and McKnight et al., U.S. Pat. No. 4,935,349, discloses a method for expressing higher eukaryotic genes in Aspergillus involving promoters capable of directing the expression of a heterologous gene in Aspergillus and other filamentous fungi. Similar techniques have been used to clone the mtr gene involved with amino acid transport in *Neurospora crassa* ("*N. crassa*") and to verify the tight linking of the cloned DNA to genomic markers flanking this gene in vivo. Stuart, W. D. et al., *Genome* (1988) 30:198–203; Koo, K. and Stuart, W. D. *Genome* (1991) 34:644–651.

Filamentous fungi possess many characteristics which make them good candidates for use in producing eukaryotic proteins. Filamentous fungi can secrete complex proteins; correctly fold three dimensional proteins including disulfide bond formation; proteolytically clip proteins following translation; and glycosylate proteins using n-linked and o-linked glycosylation reactions. These abilities have made this group of organisms attractive hosts for the production of secreted recombinant proteins.(MacKenzie, D. A. et al., *J Gen Microbiol* (1993) 139:2295–2307; Peberdy, J. F., *Trends in BioTechnology* (1994) 12:50–57). In most instances to date, commercially viable production levels of recombinant (heterologous) proteins in filamentous fungi have failed to reach the high levels of production of natural (homologous) fungal proteins. This has been attributed to a wide variety of potential causes including high levels of secreted proteases.

*Neurospora crassa* has recently been used as a host cell for recombinant homologous and heterologous protein production. (Carattoli, A., et al., *Proc Nat Acad Sci USA* (1995) 92:6612–6616; Yamashita, R. A. et al, *Fungal Genetics Newsletter* (1995 Suppl.) 42A; Kato, E. et al., *Fungal Genetics Newsletter* (1995 Suppl.) 42A; Buczynski, S. et al. *Fungal Genetics Newsletter* (1995 Suppl.) 42A). However, *Neurospora crassa* has at least 5 (five) distinct extracellular proteases, three characterized as acidic proteases, at least one neutral protease and at least one alkaline protease. (Lindberg, R. A. et al. *J Bacteriol* (1982) 150(3):1103–1108) These proteases are highly expressed under conditions of depravation of one or more essential nutrients e.g., carbon, nitrogen, sulfur and can result in a high level of protein degradation of an expressed recombinant protein. (Lindberg, R. A. et al. *J Bacteriol* (1982) 150(3):1103–1108; Cohen, L. et al., *Archiv Biochem Biophys* (1975) 169:324–330; Abbott, R. A. et al., *J Bacteriol* (1984) 159(2):505–510; Hanson, M. A. et al., *Proc Nat Acad Sci USA* 72(4):1240–1244 (1975).

Ideal host cells for use in producing recombinant proteins would have the characteristics of:

1) being simple and inexpensive to grow in laboratory cultures;

2) being able to secrete high levels of the recombinant product into liquid media thus eliminating the need to break open the host cell to recover the product, thus simplifying downstream processing protocols;

3) being able to fold, clip, glycosylate and otherwise post-translationally process the recombinant product in a manner similar or identical to the cell from which the product was originally produced in nature;

4) having a genetic marker or markers for easy identification of transformed cells, and;

5) providing a stable, non-denaturing, non-degrading environment in the production media so that the recombinant product can safely accumulate over time.

Strains of the filamentous fungus *Neurospora crassa* which are found in nature possess some, but not all, of the above characteristics. Such strains are available from stock repositories such as the Fungal Genetics Stock Center, Kansas City, Kans. Available strains possess the characteristics of:

1) being simple and inexpensive to grow in laboratory cultures;

2) being able to secrete up to 250 mg per liter of their own endogenous proteins and;

3) being able to fold, clip, glycosylate and otherwise post-translationally process their own endogenous proteins.

4) having known genetic markers which can be rescued by transformation and which are suitable for easy identification of transformed cells. The simplest of these markers are mutations which cause a single nutritional requirement and which can be rescued from the nutritional requirement by transformation with the appropriate wild-type gene (e.g., his-2, his-3, inl, trp -2);

5) having known mutations which increase the rate of secretion of some or all extracellular endogenous proteins (e.g., exo-1, unidentified allele in inl$^{rs}$ 498).

However, nowhere in nature or in collected strains, including strains containing laboratory induced mutations, are any mutations found which reduce the level of extracellular proteases normally secreted by *Neurospora crassa* into the media nor is their any strain or strains where all of the other described desirable genetic characteristics can be found nor or they found in any subset or partial combination thereof.

The present invention provides improved strains of *Neurospora crassa* methods of generating such strains, and uses thereof, for example, for use in expressing recombinant protein products. Construction of one specific strain is used by way of example but this specific illustration of the method is not intended to limit the scope of the invention.

SUMMARY OF THE INVENTION

The present invention provides improved Neurospora host cell lines for use in producing recombinant proteins.

Specifically, the present invention provides Neurospora hosts which have reduced extracellular protease activity. Such hosts are characterized by not producing a halo on sorbose gelatin agar (SGA) after at least eight days of incubation at 30° C. and are isolated by using two or more rounds of mutagenesis and selection. Such strains were found to produce secreted recombinant proteins at multiplicative rates following each round of mutagenesis and selection.

The present invention further provides improved methods of generating Neurospora host cell lines for use in producing recombinant proteins. The improved methods use two or more rounds of mutagenesis/selection to identify cell lines with reduced extracellular protease activity. In one example, an exo1/his-3 Neurospora cell line was mutagenized with UV light and colonies with a decreased capacity for producing a halo on SGA plates after four days of growth at 30° C. were selected and subjected to additional rounds of mutagenesis and selection. In one example, after three rounds of mutagenesis, cell lines were found to produce from about 27 to 125 times the amount of secreted recombinant protein as that produced by the starting strain.

The present invention further provides improved methods for producing recombinant proteins, the improvement being the use of Neurospora host cell lines selected using the methods herein described. In one example, such strains were shown to produce from about 27 to 125 times the amount of secreted recombinant protein as that produced by the starting strain.

DETAILED DESCRIPTION OF THE PREFERRED EMBODIMENTS

The present invention is based on the observation that multiple rounds of mutagenesis and selection can be used to isolate strains of Neurospora which degrade secreted recombinant proteins at a rate less than wild-type Neurospora strains and strains of Neurospora subjected to a single round of mutagenesis and selection. In one example, strains were produced which secrete recoverable recombinant proteins at a rate of approximately 27 to 125 times that seen in the starting strain. Based on this observation, the present invention provides methods of isolating improved Neurospora host cell lines which can be used for the commercial production of proteins and improved Neurospora host cell lines isolated by the disclosed method. In detail, an improved Neurospora host line having a reduced capability to degrade secreted recombinant proteins can be isolated by mutagenising a Neurospora strain, selecting clonal colonies which have reduced secreted protease activity, and then repeating the mutagenesis/selection process for one or more rounds.

As used herein, a Neurospora strain refers to filamentous fungi of the genus Neurospora. Examples of Neurospora species which can be modified as herein described include, but are not limited to *Neurospora crassa, N. africana, N. celata, N. discreta, N. dodgei, N. galapagosensis, N. intermedia, N. lineolata, N. pannonica, N. sitophila, N. sublineolata, N. terricola,* and *N. tetraserma.*

Any Neurospora strain can be used as a starting material for the present method. Suitable strains are available from the Fungal Genetics Stock Center (FGSC), Department of Microbiology, University of Kansas Medical Center, Kansas City, Kans. 66103, or the American Type Culture Collection (ATCC), 12301 Parklawn Drive, Rockville, Md. 20852. The preferred starting strain will carry a nutritional auxotrophic mutation which can be corrected by a single gene. A complementable auxotrophic mutation provides a selectable marker for use in transformation of the generated host. In the Examples which follow, a histidine auxotrophic strain was used as starting material. The strain contained a his-3 mutation which is readily complementable with a cloned wild-type his-3 gene. A discussion of various selectable markers is provided below.

A variety of methods can be used to mutagenize the Neurospora starting strain to produce a host with improved protein production capabilities. Mutations can be made using either non-directed or directed methods. A mutation is said to be non-directed when the mutagenesis method employed does not target a specific gene sequence or chromosomal location. Non-directed mutagenesis procedures which can be used to produce improved Neurospora hosts include, chemical and physical mutagenesis methods, and combinations thereof. Examples of physical mutagenesis methods include, but are not limited to UV irradiation, Davis et al., *Methods of Enzymology* 17A:79–143 (1971). In the Examples which follow, Neurospora were mutagenized using ultra violet irradiation. A skilled artisan can readily appreciate that physical modification methods can be enhanced by using chemical sensitizing agents. Examples of chemical agents for use in non-directed mutagenesis include, but are not limited to EMS.

Mutagenesis is said to be directed when the mutagenesis method is directed to a specific target sequence or target region. Directed mutagenesis methods include, but are not limited to in vitro site directed mutagenesis, homologous recombination techniques and the use of transposable elements. A skilled artisan can readily adapt knockout mutagenesis procedures to selectively target genes involved in the production of secreted proteases. Many of the genes involved in the production of secreted proteases have been cloned in Neurospora. Two or more rounds of knockout mutagenesis can be used to produce the improved host of the present invention. Further, combinations of directed and non-directed mutagenesis can be used.

The preferred mutagenesis method are the non-directed methods. Such methods allows one to randomly generate multiple mutations within one or more of the genes responsible for the production and secretion of active proteases without needing to know the identity or the chromosomal location of the mutagenized gene(s). Additionally, non-directed mutagenesis allows one to efficiently screen large numbers of individual clonal populations of mutagenized Neurospora.

In the present invention, Neurospora strains are mutagenized to produce a host strain which has reduced levels of activity of secreted proteases when compared to wild-type strains. A reduction in the activity of secreted proteases can be the result of: mutations within a protease gene, eliminating or reducing the activity of a particular protease, for example by generating a point or frame shift mutation within the protease coding or regulatory region; alterations in pathways leading to secretion of the protease; for example mutations within genes responsible for the transport of the protease; and alterations in the pathways responsible for inducing protease expression.

A variety of methods can be used to identify strains in which the mutagenesis method employed results in the reduction of exogenous proteases. The preferred selection method relies on the ability of Neurospora to degrade an extracellular protein substrate.

Wild-type Neurospora grown on solid media containing sorbose and an opaque protein protease substrate, for example sorbose agar-gelatin plates (SGA), grow as colonies and produce a halo surrounding the growing colony (a zone of clearing). The halo appears within one to four days after plating and represents the degradation of extracellular proteins by secreted proteases. After one round of mutagenesis, Neurospora containing mutations which alter the activity of secreted proteases will be identifiable by either a lack of such halos, or by having smaller halos present, after four days of incubation. After one or more additional rounds of mutagenesis and selection, strains can be identified which either lack such halos, or have smaller halos present, after eight days of incubation. All of the improved hosts of the present invention will be readily identifiable by the failure to produce a halo after growth for 8 days at 30° C. on sorbose-agargelatin plates.

Prior to the present invention, there has not been a description of a Neurospora strain which does not produce a halo after eight days of culture. Strains isolated after three rounds of mutagenesis/selection will produce multiplicative increases in protein production when compared to the starting strain. Strains producing 20, 30, 60, 90, 120 and as much as 125 times the recoverable secreted protein can be isolated after three rounds of mutagenesis.

A variety of plating media can be employed to select the improved host strains of the present invention. One essential media component is sorbose. Sorbose allows Neurospora to grow as single colonies when plated on solid media.

The plating media with additionally contain a protease substrate which is slightly to mostly opaque. Examples of such protease substrates include, but are not limited to gelatin agar, albumin, skim milk solids, casein and cytochrome c.

The preferred media will contain a low amount of an essential nutrient, for example carbon, nitrogen, or sulfur, or will contain one or more of these components in a form which needs to be degraded before it can enter (be transported) into a Neurospora cell. Such media have been shown to increase the production/activity of secreted proteases from Neurospora. Abbott, R. A. et al., *J Bacteriol* (1984) 159(2):505–510; Hanson, M. A. et al., *Proc Nat Acad Sci USA* 72(4):1240–1244 (1975).

The pH of the media can also be varied as a means to identify mutations within specific classes of proteases. Proteases can be classified according to the pH need for activity, for example, acidic, basic and neutral proteases. By plating mutagenized Neurospora on media with a particular pH, mutations which affect that class of proteases can be identified.

The plating/selection method used in the following examples allows one to screen a large number of clonal colonies following mutagenesis. Alternative methods can be used to identify the improved hosts of the present invention. For example, assays which directly detect the presence of secreted proteases can be used to identify Neurospora host of the present invention. Protease activity can be directly assayed from culture supernatants using methods described in the art. Alternatively the presence of a particular protease can be determined using immunological assays, such as an ELISA assay.

In the present methods, two or more rounds of mutagenesis are used. It has been observed that two or more rounds of mutagenesis are required to identify host cell lines which do not produce halos after eight days of culture at 30° C. on SGA plates. Such selection identifies strains with multiplicative increases in recoverable secreted protein production compared to starting strains. In one application the present method, a strain is isolating using two or more rounds of mutagenesis/selection prior to introducing an exogenous DNA into the cell for use in producing a heterologous protein. Alternatively, a single round of mutagenesis/selection is used prior to introducing an exogenous DNA into the cell and then one or more additional mutagenesis/selection rounds are performed after introduction of the exogenous DNA.

Once isolated, the improved Neurospora host of the present invention can be used to produce recombinant proteins. Protein production will be significantly enhanced because of the reduction of activity of secreted proteases when compared to wild-type strains.

Standard techniques for transformation of filamentous fungi and culturing the fungi are well known in the art and can be used to transform the improved hosts of the present invention for the production of recombinant proteins. An extensive review of techniques as applied to *N. crassa* is found, for example in Davis et al., *Methods Enzymol* (1971) 17A:79–143. Standard procedures are generally used for the maintenance of strains and the preparation of conidia. Mycelia are typically grown in liquid cultures for about 14 hours (25° C.), as described in Lambowitz et al., *J Cell Biol* (1979) 82:17–31. Host strains can generally be grown in either Vogel's or Fries minimal medium supplemented with the appropriate nutrient(s), such as, for example, histidine; arginine; phe, tyr, and/or trp (each about 80 µg/ml); p-aminobenzoic acid (about 2 µ/ml); and inositol (about 0.2 mg per ml).

When expression has been activated and the desired protein produced, the protein may be recovered from the culture using techniques generally recognized in the art. Since the protein is secreted into the medium, the medium can be removed and the secreted protein purified using conventional techniques such as size exclusion, ion exchange chromatography, reverse phase chromatography, differential centrifugation, and the like. Suitable protocols will depend on the nature of the protein product.

The improved host of the present invention are intended for use in producing a secreted recombinant protein. To aid in this use, the starting strain can contain an auxotrophic marker which can be complemented by a single gene or a selectable marker/selection agent can be employed. The appropriate choice of selectable marker will depend on the nature of the protein which is to produced and the nature of the starting strain. A straightforward choice might be, for example, an expression system which produces an enzyme responsible for an antibiotic resistance against an antibiotic to which the host is susceptible, such as benomyl. Alternatively, if a host is chosen with, for example, a nutritional deficiency, the wild-type gene can be used to replace the deficiency. To do so, however, requires a suitable mutant.

Although a starting strain can be prepared generally, numerous mutants of Neurospora are readily available which make the design of transformation vectors containing means for selection more diverse. For example, one very simple method for selection utilizes a strain with a requirement for a particular nutrient where the selectable marker means is provided by replacing the defective gene which accounts for this nutritional requirement. As an illustration, if a strain unable to grow in the absence of histidine is used as a starting strain, successful transformants can be selected using as a "marker" nucleic acid containing the wild-type of the gene that is defective in the mutant and growing the transformed cells on minimal media. Only the successful transformants will be able to grow in the absence of histidine. Similar mutations which result in dependence on the presence of other amino acids or other nutrients in the media are also known. In *N. crassa*, for instance, known mutants include mutants which have specific nutritional requirements. Examples of useful nutrient requirements and the relevant mutants include:

(1) amino acids such as histidine (his-1 through -7 mutants), proline (aga mutants), arginine (arg-11 mutants), citrulline (arg-11 mutants), asparagine (asn mutants), choline (chol-1 and chol-2 mutants), cysteine (cys-1 mutants), glutamine (gln-1 mutants), leucine (leu-1 through -4), lysine (lys-2, -4 and -5), methionine (mac mutants and met-6, -9 and -10 mutants), and threonine (thr-2 and -3 mutants);

(2) mixtures of aromatic amino acids, such as a mixture of p-aminobenzoic acid, tyrosine, tryptophan, and phenylalanine (required by all aro strains except aro-6, aro-7 and aro-8), a mixture of tryptophan and phenylalanine (required for aro-6 mutants), a mixture of isoleucine and valine (required for ilv-1, -2 and -3), and a mixture of phenylalanine and tyrosine (required for pt mutants).

(3) vitamins such as pantothenic acid (pan-1 mutants) and thiamine (thi-2 and thi-4 mutants);

(4) purine bases such as adenine (ad-2 through ad-4 and ad-8 mutants), hypoxanthine (ad-2 and ad-3 mutants), inosine, and guanine or guanosine (gua-1 or -2 mutants);

(5) pyrimidine bases such as uracil (pyr-1 through pyr-6);

(6) saturated fatty acids (cel mutants) or unsaturated fatty acids such as $C_{16}$ or $C_{18}$ fatty acids having a double bond in the cis conformation at either the 9- or 11- position, fatty acids with a double bond in the trans configuration at the 9-position, and fatty acids with multiple cis double bonds interrupted by methylene bridges (ufa-1 and -2);

(7) physiologically important ions such as potassium (trk);

(8) sugar alcohols such as inositol (acu mutants and inl mutants) and glycerol; and (9) other organic entities such as acetate (ace mutants), I-ketoglutarate, succinate, malate, formate or formaldehyde (for mutants), p-aminobenzoic acid (pab-1, -2 and -3 mutants), and sulfonamide (sfo mutants at 35° C).

Other selectable marker systems can also be used, such as the inclusion of genes which confer resistance to toxic substances or other detrimental culturing conditions. For example, genes encoding proteins which confer resistance to antibiotics can be used where selection is conducted on media containing the antibiotic. In the case of filamentous fungi, such antibiotics include benomyl.

The present invention further provides a host isolated by the methods herein described. An example of a host isolated with the present methods is denoted as Hep-25/24 and has been deposition at the American Type Culture Collection on 14 Dec. 1995, under the terms of the Budapest treaty as ATCC 74356. The production of the Hep-25/24 host is described in detail in the examples.

The following examples are intended to illustrate but not to limit the invention.

EXAMPLE 1

Methods and Materials

All starting strains were obtained from the Fungal Genetics Stock Center (FGSC), Department of Microbiology, University of Kansas Medical Center, Kansas City, Kans. 66103. Strains are identified by their locus name and FGSC stock number as listed in "Catalog of Strains" available from the Stock Center.

All techniques for growing, mating and recovery of progeny of Neurospora cultures follow well established methods which are well described in "Genetic and Microbiological Research Techniques for *Neurospora crassa*" by R. H. Davis, and F. J. DeSerres, Methods in Enzymology Volume 17A, 79–143, 1970.

Specific techniques for identification of recombinant products utilize standard assays developed for each particular product. These include but are not limited to standard enzyme linked immunosorbent assays (ELISA) and activity assays.

Description of construction of one expression strain of *Neurospora crassa*:

Genetic crosses

Strain exo-1 (FGSC# 2256) is an overproducer of extracellular enzymes including amylase and invertase (H. Gratzner and D. N. Sheehan, *J. Bact* 97: p544–549, 1969). Strain his-3 (FGSC#2278) requires histidine supplementation in the medium because of a mutation in a complex gene coding for multiple enzymatic activities in the histidine biosynthetic pathway of Neurospora (D. D. Perkins, et al., *Microbiological Reviews*, 46: p426–570, 1982).

Stain exo-1 was crossed with strain his-3 and double mutant progeny exo-1; his-3 were recovered. These progeny were designated hisexo and examples of both Neurospora mating types, A and a, were recovered.

One isolate called hisexo-la was grown on solid media known to induce extracellular protease production (Lindberg, R. A., et al., *J. Biol Chem* 256(2):811–814 (1981). This strain produced visible halos on sorbose-agar-gelatin plates after four days of growth at 30° C.

Mutagenesis of host strain

Mutagenesis of strain hisexo-la was accomplished by exposing a suspension of conidiaphores obtained from a solid slant culture of hisexo-la to an Ultra Violet light source (W Crosslinker, FB-UVX-1000 Fisher Scientific) for sufficient time (20 seconds) to obtain 60–80% kill from the UV exposure. The surviving cells were plated onto solid protease induction media in standard Petri plates at a dilution calculated to yield 50–100 colonies per plate. The resulting colonies were scored after 4 days of growth. Colonies with no visible halos were picked and transferred to Vogel's minimal medium agar slants (Davis and DeSerres) for further testing. Approximately 20,000 colonies were scored and 67 were selected for additional testing. One selected colony gave a stable and reproducible phenotype of no halo at day 4 and was designated Hep-25 (histidine-exoextracellular protease). Colonies of Hep-25 developed visible halos if allowed to grow for 8 days.

A second round of mutagenesis was performed as described above using Hep-25 as the starting strain and scoring for resulting colonies lacking halos after 8 days. Again approximately 20,000 colonies were scored and 52 were selected for further study. One of these gave a stable and reproducible phenotype and was designated Hep-25/24. Selection of transformants producing a recombinant protein Hep-25/24 was transformed by standard methods (Vollmer, S. J. et al. *Proc Natl Acad Sci USA* 83:4869–4873 (1986)) with a DNA sample containing plasmid pNH60 (obtained from FGSC) containing the wild-type his-3 gene sequence and a plasmid containing an Neurospora expression vector driven by the Neurospora glucoamylase gene RNA polymerase promoter (WO 95/19441, Alan Radford and University of Leeds, United Kingdom), containing a cDNA gene coding for the human kappa chain subunit of human immunoglobulin G (IgG) including the amino terminus coding for the signal recognition particle recognition site and secretion signal and terminated by the glucoamylase transcriptional stop site and poly adenylation site (Radford op cite). Transformants were selected for colonial growth on solid minimal medium supplemented with sorbose but without a histidine supplement.

Transformed cell colonies were picked with sterile glass disposable pipettes, transferred to sterile microtiter plates containing 0.45 μ filters on the bottom of the well (Millipore) covered by a sterile plastic liner to prevent leakage and grown in liquid Vogel's medium (Davis and DeSerres op cite) supplemented with 2% sorbose at 30° C. with shaking at 150 rpm. After 48 hours the plastic liner was removed and the media pulled through the bottom filters and collected into a standard microtiter plate using a manifold designed for such collection (Millipore). The plate containing the cells was stored at 4° C. while the media was assayed for presence of human kappa chain protein by a sandwich ELISA.

Cultures identified by the assay as producing high levels of kappa protein in the medium were transferred from the microtiter culture plate onto solid agar slants. In many series of parallel experiments, the percent of transformed colonies which also produce the recombinant protein varied from 10–30% of all transformants picked. As a general practice the six highest cultures are usually transferred for further study. Stable high producers are then passed through a microconidia growth stage to ensure homokaryotic nuclei in the production strain (Ebbole, D. et al., *Fungal Genetics Newsletter* 37:17–18 (1990). Microconidial subcultures were picked from colonial media in Petri plates and transferred to a new set of microtiter culture plates with filters on the bottom and grown and tested as described above for the original selection procedure. The colonies producing the highest amount of recombinant product (in this example human kappa chain as identified by ELISA) were transferred to minimal solid media in slant tubes.

Mutagenesis and selection of overproducing strains

Microconidiated strains which proved to be stable producers were put through the an additional round of the mutagenesis protocol and plated on solid minimal colonial medium. In this protocol the colonies which appeared after 2–3 days were picked onto microtiter growth/filter plates and after 2 days of growth were selected for increased production of the recombinant protein (in this case human kappa chain as identified by ELISA). Between 1 and 2% of all colonies examined displayed increased production. The 6 highest producers were tested for stability of production levels in 25 ml liquid shake cultures. The highest, stable producer was chosen as a parent strain for a second round of mutagenesis and selection as described above.

Experiments have been performed using three rounds of this selection procedure. It was found that at each level, an improvement of 3–5 fold in production levels is typical for the highest production mutants. These improvements are not additive but multiplicitive so that after three rounds of mutation and selection, the increase in recombinant protein production levels routinely range from 27 to 125 fold. An upper limit of production improvement possible by this method has not been reached although one clearly must exist as the number and type of genes controlling production and secretion of proteases and recombinant proteins must be limited by the size and complexity of the Neurospora genome.

Utilization of the developed strains as general expression hosts

Strains developed by the methods described above can be used as hosts for recombinant proteins other than the original recombinant protein used in the selection procedure. This can be effected in the following way.

If the transforming DNA for the his-3 (or other selective) locus in the original transformed cell line is targeted specifically to that locus by using standard methods of transforming only a partial sequence of the marker gene (i.e. his-3) but a partial sequence which covers the site of genomic mutation in the marker gene, then the transformed cell is likely to carry only one intact, functional, recombinant marker gene sequence. Similarly, if the recombinant cDNA gene expression cassette is flanked by long sequences of Neurospora genomic DNA, the insertion of the expression cassette is highly likely to occur as a single event at the site of the DNA which flanks the recombinant gene. Both of these possibilities are easily verified by simple Southern blots of the genomic DNA of the initial transformant using the marker and the expression cassette DNA as probes. If the flanking DNA sequence is carefully chosen so that insertion will cause mutagenesis of a non-essential but selectable gene, (e.g., am (nitrate reductase) or mtr (neutral amino acid transport) or caf (caffeine resistance) to mention but three of many potential sites (see Perkins et al. op cit)) then the insertion can be selected for as a loss of function of the flanking sequence gene.

Modified host strains with the above characteristics can then be co-transformed with a DNA mixture containing the marker gene (e.g., his-3) plasmid sequence which has been constructed to carry a small internal deletion in the coding region which therefore codes for a nonfunctional polypeptide and the wild-type genomic DNA sequence at the locus of the flanking sequence around the original cDNA (e.g., human kappa chain) gene expression cassette sequence.

Transformants would be first selected for restoration of the flanking gene sequence (i.e. reversion to am+) phenotype when grown on histidine supplemented media, then tested for loss of the his-3 wild-type function by testing for loss of the ability to grow on media not supplemented with histidine and finally, tested for the loss of the ability to produce the original recombinant product. Such a transformant would be expected to be identical to the modified host cell strain except that it now has once again lost its wild-type marker gene (e.g., his-3) and has replaced the cDNA expression construct containing the sequence of the original recombinant protein (human kappa chain) with a normal Neurospora wildtype DNA genomic sequence. Once again this expectation is verified by Southern blots using the appropriate DNA probes.

This new host cell is now ready to be transformed with a second cDNA expression construct similar to the first described in this illustration but containing a different cDNA sequence for expression (e.g., human gamma chain antibody, human tPA, human insulin, etc.). One again, initial transformants can be screened by selection for co-transformation with a functional wild-type marker sequence (e.g., his-3) as originally described above.

What is claimed is:

1. A mutant Neurospora strain produced from a parent Neurospora strain, wherein said mutant Neurospora strain is selected to produce from about 27 to 125 times the amount of recombinant protein as that produced by the parent strain.

2. An improved method for producing recombinant proteins, said improvement being the use of the host cells of claim 1.

* * * * *